May 4, 1965 H. KERRIGAN Plant Pat. 2,506
AZALEA PLANT
Filed Dec. 27, 1963
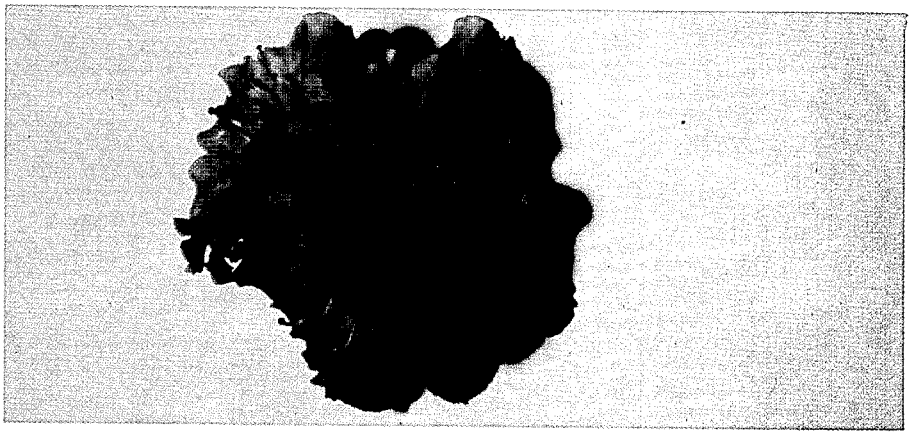
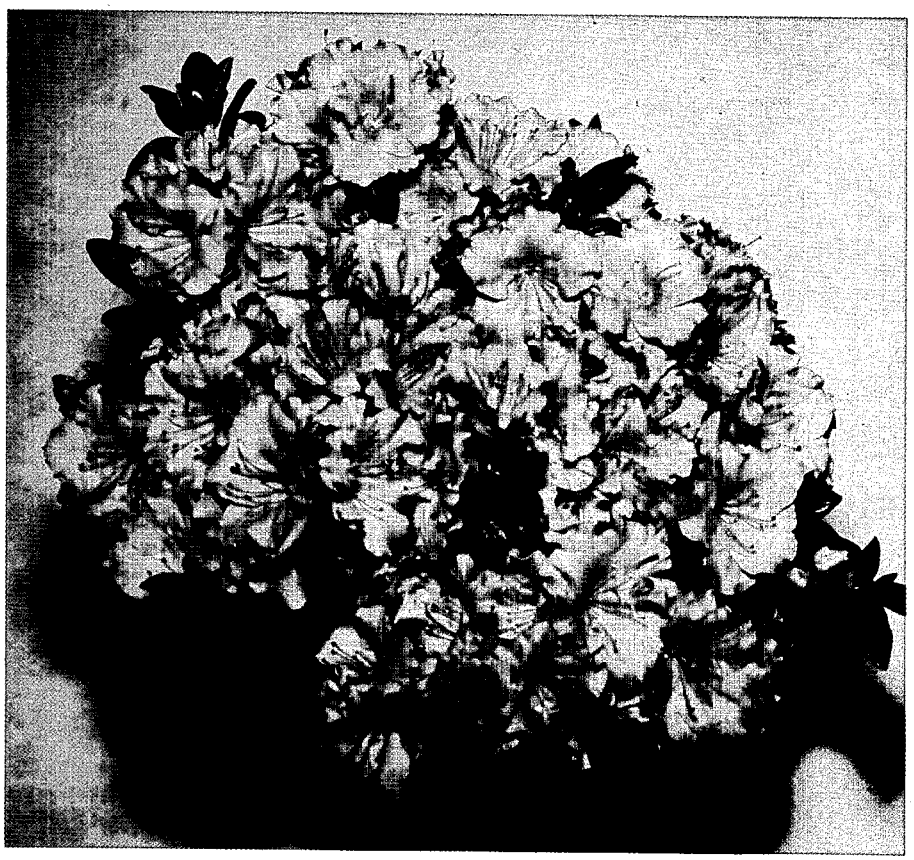

United States Patent Office

Plant Pat. 2,506
Patented May 4, 1965

2,506
AZALEA PLANT

Howard Kerrigan, 3003 Totterdell St., Oakland, Calif.

Filed Dec. 27, 1963, Ser. No. 334,063
1 Claim. (Cl. Plt.—57)

This disclosure concerns a new and distinct variety of azalea of the large flowered florists' type developed by me at Oakland, California, in 1948 as a result of a breeding program initiated by me in 1943 and carried out by me at Oakland, California.

The primary objective of this particular phase of said breeding effort was to produce an early forcing azalea intermediate between the Kurume types and the Belgian Indicas, of the desired compact habit of growth and the heavy bud setting characteristics of the Sanders hybrid "Hexe," (unpatented) but having a more rapid rate of growth than the variety "Hexe" as well as a larger flower and a more desirable shade of red, free from the crimson and magenta-cerise tonality of "Hexe."

This objective was achieved in this variety which is a hand pollinated seedling of the variety Super Orange (not patented), the seed parent fertilized with the pollen of Lentengroot (not patented), the pollen parent.

In addition to the desired improvements heretofore unknown in azaleas of this type, several other unique and distinguishing characteristics exist. My new variety of azalea differs from the pollen parent "Lentengroot" in that my variety has larger flowers the color of which is rich Turkey Red (HCC 721/3) while that of the pollen parent is Fuchsine (HCC 625). In comparison with the seed parent "Hexe," the same pronounced improvement in color is apparent. The increased size of the flower when compared with "Hexe" is also pronounced, the individual flowers of my variety being approximately twice the size of those of "Hexe." While there is a marked similarity in plant habit between my new variety and "Hexe," the rate of growth of my variety is approximately twice that of "Hexe." Moreover, both hoses of my new variety are conspicuously marked, resulting in a more spectacular effect in the finished plant at the time of marketing. The intensity and fidelity of rich red color in combination with the perfection of the calycine hose and the durability of the flower and its ability to remain on the plant for an unusually long time sets this variety apart from all others in the red color range.

These characteristics have all been proven consistent and stable during many successive generations of asexually produced plants which have been propagated by me from cuttings at Oakland, California, since 1951.

The accompanying drawing shows details of my variety of azalea and illustrates in general its distinctive horticultural characteristics substantially as they appear in nature and as accurately as present techniques will allow.

The following are detailed horticultural and botanical descriptions of my new variety of azalea plant. The color designations are those employed in the Horticultural Colour Chart issued by Wilson Colour Ltd. in collaboration with the Royal Horticultural Society.

*Horticultural description*

Semi-evergreen, small shrub of the florists' forcing type, of dense compact growth, producing a profusion of rich red flowers of Turkey Red (HCC 721/3). The foliage is abundant, dark green (HCC Ivy Green 0001060/3), very shiny on the upper surface, and light green (HCC Spinach Green o960/3) on the lower surface. The leaves are medium sized, 1⅜ inches to 2 inches long, and 1¼ inches to 1½ inches wide, egg shaped. The young foliage is Spinach Green above and below (HCC o960/3), usually somewhat lighter on the lower surface. The terminal flowering buds are pointed, brownish and enclosed in several scales. The flowering buds are rose bud shaped. Each inflorescence bears from 2–4 flowers. The bud color is Crimson (HCC 22). The flower is of the hose-in-hose type. The outer hose is perfect, never ragged or distorted. The mature flower is about 1½ inches deep and 2⅝ inches across. The flower is of the formal type, broad, flat but with slightly wavy edges to the lobes. The color is Turkey Red (HCC 721/3) with very little change in color as the flower ages. The flower is retained on the plant for 7–10 days after fully open. The faint Tyrian Purple (HCC 727) markings on the upper three flower lobe bases add to the richness of the color. The stamens are normally 8, Turkey Red, slightly darker than the petals, slender and gracefully curved. The style is about as long as the flower, Turkey Red, slender and curved. The blooming habit is seasonal and profuse. The variety can be forced for Christmas but is best when forced in the early spring. Natural blooming period is early spring. The variety is extremely fast growing and cuttings strike readily. Growth on its own roots is sufficiently rapid to enable the production of finished plants with heads 6–8 inches in diameter in two years and finished own root tree forms with 18–24 inch standards and a finished head of 6–8 inches in diameter in three years.

*Botanical description*

Dense, compact, low growing, spreading, semi-evergreen shrub 24–30 in. tall and about as wide. The stems green, rufescent moderately hirsute. The pubescence is strigose, long-lanceolate, reddish brown with lighter margins. The older stems reddish brown, striated with persistent strigose pubescence. The inflorescence is umbellate with from 4–6 buds of which 1–2 normally abort. The flower buds are Crimson, plicate, urceolate. The pedicels are ¼ inch to ½ inch long with reddish strigose pubescence. The calyx is Turkey Red, 1⅜ inches deep and 2½ inches wide, slightly zygomorphic and spotted with Crimson at the base of the dorsal three lobes and in the upper part of the tube. The lobes are auriculate, slightly undulate, all essentially equal in size, 1⅝ inches long and as broad. The corolla is essentially identical with the calyx, slightly broader and with somewhat more spotting and lacking pubescence on the reverse of the limbs and tube. The stamens, are Turkey Red, slender, curved, spreading and slightly exserted, generally 8 in number. The anthers are small, brown and normal, dehiscing through terminal pores. The pollen is sulfur yellow and is discharged enmeshed in a tapetal reticulum. The pistil is solitary, 1½ inches long. The stigma is capitate, not conspicuously lobed, rich Turkey Red and about three times as broad as the style. The style is slender, Turkey Red, 1¼ inches long, equal in diameter throughout its length except for a slight flaring at the base, sigmoid, abruptly curving upward in the distal third of its length, positioning the stigma horizontally. The ovary is normal for the species, heavily setose, light Turkey Red in color with the pigment concentrated in the bases of the setae. The seate are white, hyaline, slender and pointed. The ovary is vasiform with a slightly flanged neck. Petaloids are rare. The foliage is ovate, petiolate, entire, mucronate, dark green and subnitid above, light green and pubescent below. The midvein is prominent below as are the major secondary veins. The main veins of the leaf are visible above but the leaf surface is smooth. The margin of the leaf is moderately ciliate. The hairs are long, slender, pointed and rufescent. The upper surface of the leaf is sparsely pubescent, the hairs are reddish-brown. The lower surface of the leaf is moderately pubescent. The hairs are reddish-brown. The apex of the leaf is bluntly mucronate, light green or white.

Having disclosed my invention in the above descriptions and in the accompanying drawing what I claim is new and patentable is:

A new and distinct variety of azalea of the florists' forcing type derived from complex hybrid derivatives of *Rhododendron simsii* and related species of the *R. obtusum* complex, primarily characterized by its deep red color which is unique in its class, by the constancy and fidelity of its color under forcing conditions and on aging, by the perfection of the hose in hose flower in which the outer hose is never incomplete or ragged, by the broad classical flower form, by the unusually long life of the flower and its retention in a fresh condition on the plant which is ordinarily from 7–10 days after the flower opens, by its profuse bloom and ease of forcing for late winter and early spring use, by its ease of propagation on its own roots and especially by the extremely rapid growth which it makes on its own roots.

No references cited.

ABRAHAM G. STONE, *Primary Examiner.*